United States Patent
Vriesema et al.

(10) Patent No.: US 9,168,267 B2
(45) Date of Patent: Oct. 27, 2015

(54) **URONIC ACID AND PROBIOTICS OF *LACTOBACILLUS PARACASEI* AND *BIFIDOBACTERIUM BREVE* FOR IN VIVO TREATMENT OF INFECTION**

(75) Inventors: Adrianus Johannes Maria Vriesema, Houten (NL); Jan Knol, Wageningen (NL); Bernd Stahl, Rosbach (DE)

(73) Assignee: N.V. Nutricia, Zoetermeer (NL)

( * ) Notice: Subject to any disclaimer, the term of this patent is extended or adjusted under 35 U.S.C. 154(b) by 2105 days.

(21) Appl. No.: 11/912,084

(22) PCT Filed: Apr. 18, 2006

(86) PCT No.: PCT/NL2006/050088
§ 371 (c)(1),
(2), (4) Date: Jan. 29, 2008

(87) PCT Pub. No.: WO2006/112714
PCT Pub. Date: Oct. 26, 2006

(65) Prior Publication Data
US 2008/0199446 A1    Aug. 21, 2008

(30) Foreign Application Priority Data
Apr. 21, 2005   (EP) .................................. 05103247

(51) Int. Cl.
  *A61K 31/702* (2006.01)
  *A61K 35/745* (2015.01)
  *A61K 35/747* (2015.01)
  *A23L 1/30* (2006.01)

(52) U.S. Cl.
  CPC ............. *A61K 31/702* (2013.01); *A23L 1/3014* (2013.01); *A61K 35/745* (2013.01); *A61K 35/747* (2013.01)

(58) Field of Classification Search
  CPC ............ A61K 2300/00; A61K 35/745; A61K 31/702; A61K 35/747; A61K 35/744; A61K 38/017; A61K 31/733; A61K 31/202; A61K 31/7068; A61K 31/7072; A61K 31/7076; A61K 31/708; A61K 31/732; A61K 31/734; A61K 35/74; A23V 2002/00; A23V 2250/28; A23V 2200/3204; A23V 2200/3202; A23V 2200/32; A23V 2200/324; A23V 2200/30; A23V 2250/1882; A23V 2250/0616; A23V 2250/5062; A23V 2250/5424; A23V 2250/0634; A23V 2250/1868
  See application file for complete search history.

(56) References Cited

U.S. PATENT DOCUMENTS 8,252,769 B2 * 8/2012 van Tol et al. ................. 514/54

FOREIGN PATENT DOCUMENTS

| JP | 2004 182609 A | 7/2004 |
| WO | WO 2004/000340 A | 12/2003 |
| WO | WO-2004/089115 A1 | 10/2004 |
| WO | WO 2005/039319 A | 5/2005 |

OTHER PUBLICATIONS

International Search Report for PCT/NL2006/050088, dated Feb. 5, 2007, 2 pages.
Patent Abstracts of Japan, vol. 2003, No. 12, Dec. 5, 2003.

* cited by examiner

*Primary Examiner* — Debbie K Ware
(74) *Attorney, Agent, or Firm* — Gilberto M. Villacorta; Sunit Talapatra; Foley & Lardner LLP

(57) ABSTRACT

The present invention relates to compositions containing probiotic bacteria and uronic acid oligosaccharides. The compositions can suitably be used as infant nutrition and advantageously reduce the incidence of infection.

15 Claims, No Drawings

URONIC ACID AND PROBIOTICS OF *LACTOBACILLUS PARACASEI* AND *BIFIDOBACTERIUM BREVE* FOR IN VIVO TREATMENT OF INFECTION

FIELD OF THE INVENTION

The present invention relates to a composition containing probiotic and prebiotic nutritional components, which can suitably be used as an infant nutrition. The composition reduces the incidence of infection.

BACKGROUND OF THE INVENTION

Infant formula generally aim to mimic the compositional features and (protective) effects of human breast milk. One major step forward in this development is the inclusion of prebiotic fiber in the infant formula. Prebiotic fiber is also present in human breast milk and stimulates a healthy development of the intestinal flora. It was also recently found that oral ingestion of prebiotic fibers by infants stimulates the development of a healthy immune system. A further recent development is the inclusion of probiotic bacteria in infant formula. Many studies suggest beneficial effects of the oral administration of probiotic bacteria.

Significant research is presently conducted to find optimal combinations of probiotic bacteria and prebiotic fiber (synbiotic compositions). WO2004/089115 describes a composition comprising a *Lactobacillus* strain and a non-digestible oligosaccharide. WO2004/00340 also describes synbiotic compositions.

SUMMARY OF THE INVENTION

In one aspect the present invention relates to a method for restoring the gastrointestinal flora, maintaining gastrointestinal health and preventing e.g. infections. It was found that uronic acid oligosaccharides and probiotic bacteria synergistically improve intestinal flora, particularly in subjects having a damaged intestinal flora or an intestinal flora that is developing. Such unbalanced intestinal flora are particularly widespread among infants and patients which have been subjected to for example surgery or antibiotic treatment.

Oral ingestion of short chain uronic acid oligosaccharides reduces the adherence of pathogenic bacteria to the epithelium of the intestinal tract, and thereby reduces the occurrence of infection. Oral ingestion of these oligosaccharides is particularly advantageous for subjects, which are susceptible to infections by pathogens, for example subjects with a frail physiological state or a developing intestinal flora.

However, when only adherence of pathogenic bacteria is reduced, the pathogenic bacteria may remain and colonize the intestinal tract. Hence, advantageously, the reduced adherence should coincide with a restoration of the intestinal flora and a reduced occurrence of colonisation of the intestinal tract by pathogenic bacteria (i.e. increasing the colonisation resistance). The colonisation resistance for pathogenic bacteria can be increased by administration of probiotic bacteria. The probiotic bacteria reduce the nutrient availability thereby reducing the growth rate of present pathogenic bacteria and occupy the intestinal adherence sites for the pathogenic bacteria.

Additionally it was found that both probiotic bacteria and the uronic acid oligosaccharides stimulate the systemic immune system.

Hence the present invention provides a composition of uronic acid oligosaccharide and probiotic bacteria which can be advantageously used for maintaining and restoring gastrointestinal health; can suitably be used to prevent infection in subjects suffering a wide variety of diseases wherein a disbalanced gastrointestinal flora is present; and is particularly useful in subjects with a developing gastrointestinal flora such as infants.

Hence in one aspect the present invention provides an infant nutrition which supports the healthy development of the intestinal flora of an infant.

In a further aspect the present invention provides a composition which can be suitably used for the treatment and/or prevention of infection in patients suffering from allergy, allergic rhinitis, food hypersensitivity, atopic dermatitis, eczema, asthma, diarrhoea, infectious and antibiotic associated diarrhoea, constipation, intestinal cramps, colics, acquired immunodeficiency syndrome, cancer diabetes, cystic fibrosis, patients undergoing surgery, patients undergoing anticancer therapy and/or patients suffering from injuries caused by heat, friction, electricity, radiation, or chemicals.

The present invention is further improved by combing the uronic acid oligosaccharides and probiotic bacteria with a prebiotic oligosaccharide. The prebiotic oligosaccharide further potentiates the combination of probiotic bacteria and uronic acid oligosaccharides by stimulating the growth of the desired good indigenous flora, particularly *Lactobacilli* and *Bifidobacteria*, and helps survival and provides nutrients of the ingested probiotic bacteria. The prebiotic oligosaccharides thus specifically stimulate the prevalence of the good intestinal bacteria.

DETAILED DESCRIPTION OF PREFERRED EMBODIMENTS

The present invention provides a composition comprising probiotic bacteria and 25 to 100 wt. % uronic acid oligosaccharide with a DP of 2 to 250 based on total weight of uronic acid in the composition.

Probiotic Material

The present composition contains probiotic bacteria. Probiotic bacteria are provided as a mono- or mixed culture of live microorganisms, that when applied to man or animal, beneficially affects the host by improving the properties of the intestinal flora. Preferably, the present composition contains $10^2$ to $10^{12}$, more preferably from $10^4$ to $10^{11}$, most preferably from $10^7$ to $5 \times 10^{10}$ colony forming units (cfu) of probiotic bacteria per gram uronic acid oligosaccharide with a DP between 2 and 250, preferably DP between 2 and 100. The present composition preferably contains $10^2$ to $10^{13}$ colony forming units (cfu) of probiotic bacteria per gram dry weight of the present composition, preferably $10^2$ to $10^{12}$, more preferably $10^5$ to $10^{10}$, most preferably from $10^4$ to $1 \times 10^9$ cfu. The dosage of probiotic bacteria according to the present invention is preferably between $10^2$ to $10^{13}$, more preferably from $10^5$ to $10^{11}$, most preferably from $10^8$ to $5 \times 10^{10}$ colony forming units (cfu) per day.

Preferably the present composition contains bacteria of the genus *Lactobacillus* or *Bifidobacterium* or the present composition contains bacteria of the genus *Lactobacillus* and *Bifidobacterium*. Preferably the composition contains a *Bifidobacterium* selected from the group consisting of *B. longum, B. breve, B. infantis, B. animalis, B. lactis* and *B. bifidum*, most preferably *B. breve*. Preferably the present composition contains a *Lactobacillus* selected from the group consisting of *L. casei, L. paracasei, L. rhamnosus, L. acidophilus, L. fermentum* and *L. plantarum*. Most preferably the present composition comprises *Bifidobacterium breve* and/or *Lactobacillus paracasei*, because the present inventors have found that the growth of these bacteria in impaired in the intestine of formula fed infants compared to breast fed infants.

*Bifidobacterium breve* is a Gram-positive, anaerobic, rod-shaped bacterium. The present *B. breve* preferably has at least 95% identity of the 16 S rRNA sequence when compared to the type strain of *B. breve* ATCC 15700, more preferably at least 97% identity as defined in Stackebrandt & Goebel, 1994, Int. J. Syst. Bacteriol. 44:846-849. Nucleic acid sequence identity is preferably calculated for two nucleotide sequences, when optimally aligned, using the programs GAP or BESTFIT using default parameters. The GAP default parameters are used, with a gap creation penalty=50 (nucleotides)/8 (proteins) and gap extension penalty=3 (nucleotides)/2 (proteins). For nucleotides the default scoring matrix used is nwsgapdna (Henikoff & Henikoff, 1992, PNAS 89, 915-919). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752, USA or EMBOSSwin v. 2.10.0.

The *Bifidobacterium* used in the present invention preferably gives a signal with the 5' nuclease assay method as described in co-pending international patent application PCT/NL2004/000748 and european patent application 05075486.0 of the present applicant. According to a preferred embodiment, the present composition contains at least one *B. breve* selected from the group consisting of *B. breve* Bb-03 (Rhodia), *B. breve* M16-V (Morinaga), *B. breve* R0070 (Institute Rosell, Lallemand), DSM 20091, and LMG 11613. Most preferably, the *B. breve* is *B. breve* M-16V (Morinaga).

In a preferred embodiment the present composition comprises *Lactobacillus paracasei*. Preferably the present *L. paracasei* strain has at least 95, more preferably at least 97% identity of the 16S rRNA sequence when compared to the type strain of *L. paracasei* ATCC 25032 as defined above. The *Lactobacillus* used in the present invention preferably gives a signal with the 5' nuclease assay method as described in the co-pending european patent application of the present applicant with application no. 05075486.0. According to a preferred embodiment, the present composition contains at least a *L. paracasei* selected from the group consisting of *L. paracasei* F19 (Arla, Sweden), *L. paracasei* LAFTI L26 (DSM Food Specialties, the Netherlands) and *L. paracasei* CRL 431 (Chr. Ilansen, Denmark), LMG 12165 and LMG 11407.

Uronic Acid Oligosaccharide

The present composition contains between 25 and 100 wt. %, preferably between 50 and 100 wt. % uronic acid oligosaccharide with a degree of polymerization (DP) of 2 to 250 based on total weight of uronic acid in the composition. Preferably the present composition contains between 25 and 100 wt. %, preferably between 50 and 100 wt. % uronic acid oligosaccharide with a degree of polymerization (DP) of 2 to 100 based on total weight of uronic acid in the composition. More preferably, the present composition contains between 25 and 100 wt. % galacturonic acid oligosaccharide with a DP of 2 to 250 based on total weight of uronic acid in the composition, more preferably between 25 and 100 wt. % galactlironic acid oligosaceharide with a DP of 2 to 100 based on total weight of uronic acid in the composition, even more preferably between 25 and 100 wt. % galacturonic acid oligosaccharide with a DP of 2 to 50 based on total weight of uronic acid in the composition.

The term uronic acid oligosaccharide as used in the present invention refers to an oligosaccharide wherein at least 50% of the residues are selected from the group consisting of guluronic acid, mannuronic acid, galacturonic acid and glucuronic acid. In a preferred embodiment the uronic acid oligosaccharide contains at least 50% galacturonic acid based on total uronic acid residues in the uronic acid oligosaccharide. More preferably, the present uronic acid oligosaccharide is hydrolysed pectin, preferably polygalacturonic acid, even more preferably prepared by hydrolysis of apple, citrus and/or sugar beet pectin.

In a preferred embodiment, the uronic acid oligosaccharides of the present invention contains between 25 and 100 wt. % galacturonic oligosaccharides with a DP between 2 and 100 based on total weight of galacturonic acid, more preferably between 50 and 100 wt. %, even more preferably between 75 and 100 wt. %. Preferably the composition contains between 25 and 100 wt. % galacturonic oligosaccharides with a DP between 2 and 50 based on total weight of galacturonic acid, more preferably between 50 and 100 wt. %, even more preferably between 75 and 100 wt. %.

The galactoronic acid oligosaccharides are preferably prepared by enzymatic digestion of pectin with pectin lyase, pectic lyase, endopolygalacturonase and/or pectinase. The present uronic acid oligosaccharide is preferably obtainable by enzymatic digestion of pectin with pectin lyase, pectic lyase, endopolygalacturonase and/or pectinase.

The uronic acid oligosaccharide may be methoxylated and/or amidated. The uronic acid oligosaccharide is preferably indigestible in the upper human intestinal tract and water-soluble.

In a preferred embodiment, at least one of the terminal hexose units of the uronic acid oligosaccharide has a double bond, which is preferably situated between the $C_4$ and $C_5$ position of the terminal hexose unit. The double bond provides effectively protects against attachment of the pathogenic bacteria to the epithelium. Preferably one of the terminal hexose units comprises the double bond. The double bond at terminal hexose unit can for example be obtained by enzymatically hydrolyzing pectin with lyase.

Preferably the uronic acid oligosaccharide has the structure I below, wherein the terminal hexose (left) preferably comprises a double bond. The hexose units other than the terminal hexose unit(s) are preferably uronic acid units, preferably galacturonic acid units. The carboxylic acid groups on these units may be free or (partly) esterified, and preferably at least 10% is methylated (see below).

Structure I: Polymeric Acid Oligosaccharide

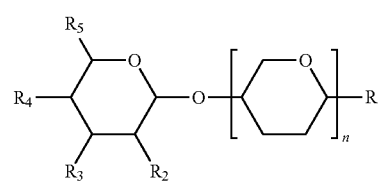

wherein:

R is preferably selected from the group consisting of hydrogen, hydroxy or acid group, preferably hydroxy; and at least one selected from the group consisting of $R_2$, $R_3$, $R_4$ and $R_5$ represents N-acetylneuraminic acid, N-glycoloylneuraminic acid, free or esterified carboxylic acid, sulfuric acid group or phosphoric acid group, and the remaining of $R_2$, $R_3$, $R_4$ and $R_5$ representing hydroxy and/or hydrogen. Preferably one selected from the group consisting of $R_2$, $R_3$, $R_4$ and $R_5$ represents N-acetylneuraminic acid, N-glycoloyl-neuraminic acid, free or esterified carboxylic acid, sulfuric acid group or phosphoric acid group, preferably a free or esterified carboxylic acid, and the remaining represent hydroxy and/or hydrogen. Even more preferably one selected from the group consisting of $R_2$, $R_3$, $R_4$ and $R_5$ represents free or esterified carboxylic acid and the remaining of $R_2$, $R_3$, $R_4$ and $R_5$ representing hydroxy and/or hydrogen; and n is an integer and refers to a number of hexose units (see also Degree of Polymerisation, below), which may be any hexose unit. Suitably n is an integer between 1-249, preferably between 1 and 99, more preferably between 1 and 49. Preferably the hexose unit(s) is a uronic acid unit.

Most preferably R, $R_2$ and $R_3$ represent hydroxy, $R_4$ represent hydrogen, $R_5$ represents carboxylic acid, n is any number between 1 and 99, preferably between 1 and 50, most preferably between 1 and 10 and the hexose unit is preferably galacturonic acid.

More preferably, the present uronic acid oligosaccharide has a structure according to FIG. 2.

FIG. 2: Preferred Terminal Hexuronic Acid Group

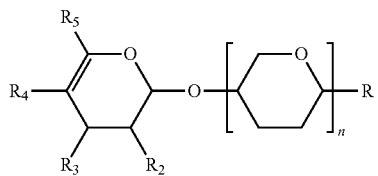

wherein;

R is preferably selected from the group consisting of hydrogen, hydroxy or acid group, preferably hydroxy (see above); and at least one selected from the group consisting of $R_2$, $R_3$, $R_4$ and $R_5$ represents N-acetylneuraminic acid, N-glycoloyl-neuraminic acid, free or esterified carboxylic acid, sulfuric acid group and phosphoric acid group, and the remaining of $R_2$, $R_3$, $R_4$ and $R_5$ representing hydroxy and/or hydrogen. Preferably one selected from the group consisting of $R_2$, $R_3$, $R_4$ and $R_5$ represents N-acetylneuraminic acid, N-glycoloyl-neuraminic acid, free or esterified carboxylic acid, sulfuric acid group and phosphoric acid group, and the remaining of $R_2$, $R_3$, $R_4$ and $R_5$ represent hydroxy and/or hydrogen. Even more preferably one selected from the group consisting of $R_2$, $R_3$, $R_4$ and $R_5$ represents free or esterified carboxylic acid and the remaining of $R_2$, $R_3$, $R_4$ and $R_5$ represent hydroxy and/or hydrogen; and n is an integer and refers to a number of hexose units (see also Degree of Polymerisation, below), which may be any hexose unit. Suitably n is an integer between 1-249 (preferably between 1 and 99, even more preferably 1 to 49) representing the number of hexose units said hexose units preferably being uronic acid, even more preferably being galacturonic acid units. The carboxylic acid groups on these units may be free or (partly) esterified, and are preferably at least partly methylated.

Most preferably, $R_2$ and $R_3$ represent hydroxy, $R_4$ represent hydrogen and $R_5$ represents free or esterified carboxylic acid.

In a further embodiment, a mixture of uronic acid oligosaccharides is used, which have a different DP and/or comprise both unsaturated and saturated terminal hexose unit. Preferably at least 5%, more preferably at least 10%, even more preferably at least 25% of the terminal hexuronic units of the uronic acid oligosaccharide unsaturated hexuronic unit (see e.g. FIG. 2). As each individual uronic acid oligosaccharide preferably comprises only one unsaturated terminal hexuronic unit, preferably less than 50% of the terminal hexuronic units is an unsaturated hexuronic unit (i.e. comprises a double bond).

A mixture of uronic acid oligosaccharides preferably contains between 2 and 50% unsaturated hexuronic units based on the total amount of hexuronic units, preferably between 10 and 40%.

The uronic acid oligosaccharide can be derivatised. In one embodiment the uronic acid oligosaccharides are characterized by a degree of methoxylation above 20%, preferably above 50% even more preferably above 70%. As used herein, "degree of methoxylation" (also referred to as DE or "degree of esterification") is intended to mean the extent to which free carboxylic acid groups contained in the polygalacturonic acid chain have been esterified (e.g. by methylation). In another embodiment the uronic acid oligosaccharides have a degree of methylation above 20%, preferably above 50% even more preferably above 70%.

Concentration Uronic Acid Oligosaccharides

The present composition is preferably a nutritional composition, containing fat, digestible carbohydrate and protein. The present nutritional composition preferably contains between 0.01 and 5 grams uronic acid oligosaccharide with a DP of 2 to 250 per 100 gram dry weight of the nutritional composition, more preferably between 0.05 and 2 grams per 100 gram dry weight. The present nutritional composition preferably contains between 0.01 and 5 grams galacturonic acid oligosaccharide with a DP of 2 to 250 (preferably DP of 2-100) per 100 gram dry weight of the nutritional composition, more preferably between 0.05 and 2 grams per 100 gram dry weight.

The present method preferably comprises the administration of between 0.05 and 10 grams uronic acid oligosaccharide with a DP of 2 to 100 per day, even more preferably between 0.1 and 5 grams uronic acid oligosaccharides per day.

Prebiotic Fiber

In addition to the uronic acid oligosaccharide and the probiotic bacteria, the present composition preferably comprises prebiotic fiber, which stimulate the growth of the intestinal probiotic bacteria, particularly *Bifidobacteria* and/or the *Lactobacilli*. Advantageously, the prebiotic fibers are at least 50% water-soluble oligosaccharides (L. Prosky et al, J. Assoc. Anal. Chem 71: 1017-1023, 1988) with a degree of polymerization (DP) of 2-100 which preferably do not contain uronic acid. The oligosaccharides lacking uronic acid units are hereinafter referred to as "indigestible oligosaccharide". The indigestible oligosaccharide are not or only partially digested in the intestine by the action of acids or digestive enzymes present in the human upper digestive tract (small intestine and stomach) and are fermented by the human intestinal flora. For example glucose, fructose, galactose, sucrose, lactose, maltose and the maltodextrins are considered digestible.

The indigestible oligosaccharide is preferably a mixture of non-digestible saccharides. This is common practise, because the use of indigestible oligosaccharides with e.g. one chain length is very expensive. Preferred examples of commercially available mixtures of indigestible oligosaccharides are inulin, fructooligosaccharide and galactooligosaccharide. When the indigestible oligosaccharide is a saccharide mixtures, the averages of the respective parameters are used for defining the present invention. For example if saccharide A is a mixture of individual saccharides 25 wt. % Glu-Gal-Gal-Gal, 25 wt. % Glu-Gal-Gal and 50 wt. % Gal-Gal, the average monosaccharide composition is 85.4% Gal and 14.6% Glu. The average degree of polymerisation (DP) is 2.75.

The degree of polymerisation of the indigestible oligosaccharide is preferably below 60, more preferably below 40, even more preferably below 20, most preferably below 10. The oligosaccharide preferably comprises at least 60%, more preferably at least 95% hexose units selected from the group consisting of fructose, galactose and glucose.

Preferably the indigestible oligosaccharide is selected from the group consisting of: cellobiose (4-O-β-D-glucopyranosyl-D-glucose), cellodextrins ((4-O-β-D-glucopyranosyl)$_n$-D-glucose), B-cyclodextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructofuranoside), D-agatose, D-lyxo-hexulose, lactosucrose (O-β-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-(-D-glucopyranosyl-β-D-fructofuranoside), β-galactooligosaccharides or transgalacto-oligosaccharides (β-D-galactopyranosyl-(1-6)-[β-D-glucopyranosyl]$_n$-(1-4) α-D glucose), lactulose (4-O-β-D-galactopyranosyl-D-fructose), 4'-galatosyllactose (O-D-galactopyranosyl-(1-4)-O-β-D-glucopyranosyl-(1-4)-D-glucopyranose), synthetic galactooligosaccharide (neogalactobiose, isogalactobiose, galsucrose, isolactosel, II and III), fructans—Levan-type (β-D-(2→6)-fructofuranosyl)$_n$ α-D-glucopyranoside), fructans—Inulin-type(β-D-((2→1)-fructofuranosyl)$_n$ α-D-glucopyranoside), 1f-β-fructofuranosylnystose (β-D-((2→1)-fructofuranosyl)$_n$ B-D-fructofuranoside), xylooligosaccharides (B-D-((1→4)-xylose)$_n$, lafinose, lactosucrose, arabinooligosaccharides and mixtures thereof.

According to a further preferred embodiment the indigestible oligosaccharide is selected from the group consisting of fructans, fructooligosaccharides, indigestible dextrins galactooligosaccharides (including transgalactooligosaccharides), xylooligosaccharides, soybean oligosaccharides, arabinooligosaccharides, glucooligosaccharides, mannooligosaccharides, fructooligosaccharides and mixtures thereof.

Suitable indigestible oligosaccharides and their production methods are further described in Laere K J M (Laere, K J M, Degradation of structurally different non-digestible oligosaccharides by intestinal bacteria: glycosylhydrolases of Bi. adolescentis. PhD-thesis, June 2000, Wageningen Agricultural University, Wageningen, The Netherlands) the entire content of which is hereby incorporated by reference.

The present invention preferably provides a composition with two different indigestible oligosaccharides, i.e. indigestible oligosaccharide A and indigestible oligosaccharide B, hereinafter referred to as saccharide A and saccharide B respectively. Saccharide A and saccharide B are preferably different saccharides and have a different glycosidic linkages, degree of polymerisation and/or monosaccharide composition.

Preferably at least 98% of the total monosaccharide units of saccharide A and B are monosaccharides selected from the group consisting of galactose (gal), fructose (fru) and glucose (glu) monosaccharides. According to a preferred embodiment of the present invention, the percentage of at least one monosaccharide selected from the group consisting of glucose, fructose and galactose in saccharide A is at least 40% higher than the percentage of the same monosaccharide in saccharide B, preferably at least 50%, more preferably at least 75%, even more preferably at least 90%. An increased diversity of monosaccharides stimulates a wider population of beneficial intestinal bacteria.

The percentage of a monosaccharide in the saccharide can be simply calculated by dividing the amount of the respective monosaccharide unit (e.g. glucose) in the saccharide by the total amount of the monosaccharide units in that saccharide and multiply it by 100. When the saccharide is a saccharide mixture, the contribution of each individual saccharide in the saccharide mixture must be taken into account. The percentage of a saccharide mixture can simply be determined by completely hydrolysing the mixture and determining the molar percentage for each monosaccharide.

Preferably saccharide A contains at least 40% galactose, more preferably at least 67% galactose, more preferably at least 75 mol % galactose. Preferably saccharide B contains at least 30% fructose, more preferably at least 67% fructose, even more preferably at least 80 wt. % fructose.

For example, in the case where saccharide A is a mixture of glu-(gal)$_{n=2-7}$ (n is thus an intger selected from 2-7) with an average monosaccharide composition of 20% glucose and 80% galactose and saccharide B is a mixture of glu-(fru)$_{n=2-7}$ and (fru)$_{n=2-7}$ with an average monosaccharide composition of 10% glucose and 90% fructose, the difference in a) glucose is 10%; b) fructose is 90%; and c) galactose 80%. In this example both the fructose and galactose fulfil the criteria that the percentage of at least one monosaccharide selected from the group consisting of glucose, fructose and galactose in saccharide A is at least 40% higher that the percentage of the same monosaccharide in saccharide B.

Degree of Polymerisation

Saccharide A and B have a degree of polymerisation (DP) of 2 to 100. Preferably at least 80 wt. %, more preferably at least 95 wt. %, most preferably at least 98 wt. % of the cumulative weight of saccharide A and B has a degree of polymerisation (DP) below 60, more preferably below 40, most preferably below 20. The lower DP advantageously reduces viscosity and increases fermentability of the non-digestible saccharides. Preferably at least 50 wt. %, preferably at least 75 wt. % of the cumulative weight of saccharides A and B are non-digestible saccharides with a DP of 2-8. By using a mixture with a high weight percentage of small saccharides the fementability and stimulation effect on the growth of the lactic acid bacteria and *Bifidobacteria* will be increased.

According to a preferred embodiment of the present invention, the DP of saccharide A is al least 5 monosaccharide units lower than the degree of polymerisation of saccharide B, preferably at least 10, even more preferably at least 15. Including a saccharide with an increased degree of polymerisation reduces the osmotic load, which is advantageous for an infant nutrition and improves prebiotic stimulation of the intestinal flora also at more distal parts of the colon.

Preferably, saccharide A has a DP of 2-15, more preferably 2-8. Preferably saccharide B has DP of 8-100. The saccharides A and B with a different DP may have the same or slightly different monosaccharide composition. When saccharides A and B have different DP and similar monosaccharide composition than the difference in average DP between saccharide A and saccharide B is preferably at least 5, more preferably at least 10, even more preferably at least 15. Preferably, saccharide A and B have a different monosaccharide composition (see above) and a different DP.

For example, if saccharide A is a mixture of glu-(fru)$_{m=2-7}$ and (fru)$_{m=2-6}$ with an average DP of 3.5 monosaccharide units and saccharide B is glu-(fru)$_{n=12-100}$ with an average DP of 25 monosaccharide units; than the difference in the average DP (25−3.5=)21.5.

In a further preferred embodiment of the present invention the percentage of at least one glycosidic linkage of saccharide A based on total glycosidic linkages of saccharide A is at least 40% higher the percentage of the same glycosidic linkage in saccharide B, preferably at least 50%, even more preferably at least 75%. The term "glycosidic linkage" as used in the present invention refers to a C—O—C linkage formed between the rings of two cyclic monosaccharides by the elimination of water. An increased diversity in glycosidic linkages stimulates a wider range of beneficial bacteria.

Glycosidic linkages differ in that they covalently bind carbon atoms in the monosaccharide units at differently numbered positions, and/or that they form α or β bonds. Examples of different glycosidic linkages occurring in non-digestible saccharides are β(1,3), α(1,4), β(2,1), α(1,2), and β(1,4) linkages.

Preferably the glycosidic linkages in saccharide A comprises at least 40% [(1,4) and /or β(1,6) glycosidic linkages, more preferably at least 75%. The glycosidic linkages in saccharide B preferably comprise at least 40% β(2,1) glycosidic linkages, more preferably at least 75%.

Saccharide A is preferably a saccharide selected from the group consisting of β-galactooligosaccharides, α-galactooligosaccharides, and galactans. According to a more preferred embodiment saccharide A is β-galactooligosaccharide, more preferably transgalactooligosaccharide. Preferably saccharide A comprises β-galactooligosaccharides with β(1,4) and/or β(1,6) glycosidic bonds and a terminal glucose. Transgalactooligosaccharide is for example commercially available under the tradename Vivinal®GOS (Borculo Domo Ingredients, Zwolle, Netherlands).

Saccharide B is preferably a saccharide selected from the group consisting of fructopolysaccharides and fructooligosaccharides. The terms fructopolysaccharides, polyfructose, polyfructan and fructan are interchangeably used herein and refer to polysaccharides comprising β-linked fructose units, which are preferably linked by β(2,1) and/or β(2,6) glycosidic linkages. Preferably, the fructopolysaccharide contains a terminal β(2,1) glycosidic linked glucose. Preferably, the fructopolysaccharide contains at least 7 β-linked fructose units. In a further preferred embodiment inulin is used as saccharide B. Inulin is a type of fructopolysaccharide wherein at least 75% of the glycosidic linkages are β(2,1) linkages. Typically, inulin has an average chain length between 8 and 60 monosaccharide units. Suitable fructopolysaccharide for use in the compositions of the present invention is commercially available under the trade name. Raftiline®HP (Orafti).

In a further preferred embodiment, saccharide B is a fructooligosaccharide. A fructooligosaccharide is a saccharide comprising C-linked fructose units, which are preferably linked by β(2,1) and/or β(2,6) glycosidic linkages. The fructooligosaccharide preferably contains a β(2,1) glycosidic linked glucose at the reducing end. Preferably, the fructooligosaccharide contains 2 to 6 β-linked fructose units. A suitable source of fructooligosaccharide is Raftilose® (Orafti), or Actilight (Beghin-Meiji).

Concentration Indigestible Oligosaccharides

The present composition preferably comprises at least 5 mg indigestible oligosaccharide per 100 gram dry weight of the present composition, more preferably at least 50 mg, even more preferably at least 0.1 g, most preferably at least 0.5 g. Preferably the present composition does not contain more than 10 g indigestible oligosaccharide per 100 g dry weight of the present composition, preferably not more than 2.0 g.

The indigestible oligosaccharides according to the present invention are preferably administered in a daily dose of 0.1 to 30 g, more preferably 0.5 to 15 g, more preferably 3 to 10 g.

If the composition contains saccharide A and saccharide B, the weight ratio saccharide A/saccharide B is preferably between 0.01 and 100, more preferably between 0.5 and 100, even more preferably between 4 and 100, most preferably between 24 and 100. A high weight ratio is particularly advantageous when saccharide A has a low DP and saccharide B has a relatively high DP. It ensures an optimal equilibrium between osmolality and fermentability.

Saccharide A and saccharide B preferably comprise between 5 and 100 wt. % based on the total weight of the indigestible saccharides in the present composition, more preferably 50 to 100 wt. %.

Macronutrients

When formulated as a nutritional composition, the present composition preferably contains 5 to 16 en % protein; 35 to 60 en % fat; and 25 to 75 en % carbohydrates, preferably 5 to 12.0 en % protein; 39 to 50 en % fat; and 40 to 55 en % carbohydrates (en % is short for energy percentage and represents the relative amount each constituent contributes to the total caloric value of the preparation). This nutritional composition is particularly suitable for feeding to an infant because it provides the infant with the required nutrients.

The present composition can also be advantageously added to human milk. Products presently added to human milk are often referred to as breast milk fortifiers. Hence in a further aspect the present invention provides a composition comprising human milk and the present composition. In still a further aspect the present invention provides a method for making a nutritional composition, comprising admixing human milk and the present composition.

Preferably the present composition comprises 5 to 20 en. % protein, more preferably 8 to 12 en. %. Preferably the present composition comprises a protein selected from the group consisting of casein, whey, skim milk, soy protein, pea protein, collagen, rice protein and/or corn protein. Preferably at least 25 wt. % of the total protein of the present composition is provided by hydrolysed protein and/or free amino acid. The use of protein hydrolysate and/or free amino acids reduces side effects, such as allergy, which is particularly undesirable in infants with suboptimal intestinal flora.

Preferably, the present composition comprises zinc (Zn). Zinc protects the intestinal barrier function in the presence of pathogens (Roselli et al, 2003 J Nutr. 133:4077) and plays an important role in enterocyte proliferation. The present composition preferably contains at least 10 μg zinc per g dry weight of the composition, more preferably at least 30 μg, most preferably at least 50 μg Zn. Preferably, the present composition contains less than 0.3 mg, more preferably no more than 0.2 mg zinc per g dry weight of the present composition. Preferably zinc is added to the composition in the form of zinc sulphate, zinc acetate, zinc chloride, zinc lactate, zinc citrate, zinc gluconate and/or zinc oxide.

The present composition is preferably administered in liquid form. Stool irregularities (e.g. hard stools, insufficient stool volume, diarrhoea) are a major problem in infants with sub-optimal intestinal flora. Therefore, the present composition preferably has an osmolality between 50 and 500 mOsm/kg, more preferably between 100 and 400 mOsm/kg. With this osmolality, the present composition is particularly suitable for the treatment and/or prevention of diarrhoea. The proper osmolality in combination with the uronic acid oligosaccharides and probiotics decreases the time wherein a normal stool is redeveloped.

For the same reasons, it is also important that the present composition does not have an excessive caloric density, yet still provides sufficient calories to feed the subject. Hence, the liquid food preferably has a caloric density between 0.1 and 2.5 kcal/ml, even more preferably a caloric density of between 0.5 and 1.5 kcal/ml, most preferably between 0.6 and 0.9 kcal/ml. Optimal caloric density also contributes to the reduced occurrence of diarrhoea.

The present compositions preferably comprises minerals, trace elements and vitamins, choline, taurine, carnitine, myo-inositol and/or mixtures thereof.

Applications

The present composition is particularly useful for feeding human infants. Hence, the present invention also provides the use of the present composition for the manufacture of a nutritional composition for feeding infants. Preferably the infants have the age of 0-36 months, preferably an age between 0 and 18 months.

The composition according to the present invention has been found to be particularly useful as an infant nutrition. Also the composition is especially suitable for normalisation of the *Bifidobacterium* and/or the *Lactobacillus* population according to the species distribution in human milk-fed infants in the gastro-intestinal tract of infants which were non- or partly human milk-fed, in particular those which are prematurely born babies, maturely born babies, as well as infants which are in the adaptation period to solid food. Hence the present invention provides a method for providing nutrition to a human infant, said method comprising administering to the infant the present composition.

Thus a further aspect of the present invention concerns a food preparation comprising a composition as defined above. In one embodiment the food preparation is an infant nutrition.

The intestinal flora has an important effect on disorders such as gastrointestinal disorders, immune disorders and/or endocrine disorders. Hence, in a further aspect the present invention provides a method, the present composition can be advantageously used in the manufacture of a medicament for use in a method for the prevention and/or treatment of gastrointestinal disorder, immune disorder and/or endocrine disorders. Particularly allergy, allergic rhinitis, food hypersensitivity, atopic dermatitis, eczema, asthma, diarrhoea, infectious and antibiotic associated diarrhoea, intestinal inflammation, infection, constipation, intestinal cramps, colics, acquired immunodeficiency syndrome, cancer, cystic fibrosis and/or diabetes can be suitably treated and/or prevented with the present composition. In a preferred embodiment, the present invention provides a method for the treatment and/or prevention of allergy and/or infection. In a preferred embodiment, the present invention provides a method for the treatment and/or prevention of acquired immunodeficiency syndrome.

In a further preferred embodiment the present composition is used in a method for the treatment and/or prevention of infection in patients suffering from allergy, allergic rhinitis, food hypersensitivity, atopic dermatitis, eczema, asthma, diarrhoea, infectious and antibiotic associated diarrhoea, constipation, intestinal cramps, colics, acquired imunodeficiency syndrome, cancer diabetes, cystic fibrosis, patients undergoing surgery, patients undergoing anticancer therapy and patients suffering from injuries caused by heat, friction, electricity, radiation, or chemicals. The reduced occurrence or intensity of these diseases is due to the optimized intestinal flora, particularly the optimized *Bifidobacterium* species population and/or optimized *Lactobacillus* species population and a reduced adherence of pathogenic bacteria.

In another embodiment the present invention provides a method for the prevention of vaginal infections, said method comprising topically applying the present composition in a suitable administration form.

EXAMPLES

Example 1

Composition with Pectin Hydrolysate, Prebiotic Fiber and Probiotic Bacteria

Infant nutrition comprising per 12.6 gram powder: 1.6 gram protein, 3.6 gram fat, 6.4 gram digestible carbohydrates (mainly lactose), 0.8 gram non-digestible carbohydrates of which 0.60 gram transgalactooligosaccharides, 0.07 gram inulin (Raftilin HP, Orafti), 0.12 gram lyase hydrolysed pectin with an average degree of polymerisation of 4, and $1 \times 10^9$ cfu *Bifidobacterium breve* M-16V (Moringa) and $1 \times 10^9$ cfu *Lactobacillus paracasei* LAFTI L26 (DSM Food Specialties, the Netherlands).

The invention claimed is:
1. A nutritional composition consisting essentially of:
    (a) probiotic bacteria consisting of *Lactobacillus paracasei* and *Bifidobacterium breve*,
    (b) 25 to 100 wt. % uronic acid oligosaccharide with a degree of polymerization (DP) of 2 to 250 based on total weight of uronic acid in the composition; and
    (c) 5 to 16 en % protein, 25 to 75 en % carbohydrate and 35 to 60 en % fat.
2. The composition according to claim 1, in which the uronic acid oligosaccharide of the composition comprises 25 to 100 wt. % galacturonic acid oligosaccharide with a DP of 2 to 250 based on total weight of uronic acid in the composition.
3. The composition according to claim 1, in which the uronic acid oligosaccharide is obtained by enzymatic digestion of pectin with pectin lyase, pectic lyase, endopolygalacturonase and/or pectinase.
4. The composition according to claim 1, in which the uronic acid oligosaccharide has the following structure:

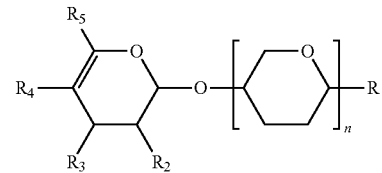

wherein;
R is selected from the group consisting of hydrogen, hydroxy or acid group; and at least one selected from the group consisting of $R_2$, $R_3$, $R_4$ and $R_5$ represents N-acetylneuraminic acid, N-glycoloylneuraminic acid, free or esterified carboxylic acid, sulfuric acid group and/or phosphoric acid group, and the remaining of $R_2$, $R_3$, $R_4$ and $R_5$ represent hydroxy and/or hydrogen; and n is an integer from 1-99.
5. The composition according to claim 1, in which the composition further comprises an indigestible oligosaccharide selected from the group consisting of fructans, fructooligosaccharides, indigestible dextrins, galactooligosaccharides, xylooligosaccharides, soybean oligosaccharides, arabinooligosaccharides, glucooligosaccharides, mannooligosaccharides, fucooligosaccharides and mixtures thereof.

6. The composition according to claim 1, in which the composition further comprises an indigestible oligosaccharide lacking uronic acid.

7. The composition of claim 1 comprising minerals, trace elements, vitamins, choline, taurine, carnitine, myo-inositol and/or mixtures thereof.

8. A method for treatment and/or reduction of the occurrence or intensity of infection in a subject comprising enterally administering to the subject a nutritional composition consisting essentially of:
  (a) probiotic bacteria consisting of *Lactobacillus paracasei* and *Bifdobacterium breve*,
  (b) 25 to 100 wt. % uronic acid oligosaccharide with a degree of polymerization (DP) of 2 to 250 based on total weight of uronic acid in the composition; and
  (c) 5 to 16 en % protein, 25 to 75 en % carbohydrate and 35 to 60 en % fat.

9. The method according to claim 8, in which the subject is suffering from allergy, allergic rhinitis, food hypersensitivity, atopic dermatitis, eczema, asthma, diarrhoea, infectious and antibiotic associated diarrhoea, constipation, intestinal cramps, colics, acquired immunodeficiency syndrome, cancer diabetes, cystic fibrosis; injuries caused by heat, friction, electricity, radiation, or chemicals; and/or the subject is undergoing surgery or anticancer therapy.

10. The method according to claim 8, in which the uronic acid oligosaccharide is hydrolyzed pectin.

11. The method according to claim 8, in which the composition further comprises fructans, fructooligosaccharides, indigestible dextrins, galactooligosaccharides, xylooligosaccharides, soybean oligosaccharides, arabinooligosaccharides, glucooligosaccharides, mannooligosaccharides, fucooligosaccharides and mixtures thereof.

12. The method according to claim 11, in which the galactooligosaccharides comprise transgalactooligosaccharides.

13. The method according to claim 8, in which the subject is a human infant.

14. The method according to claim 8, in which the subject has been subjected to surgery or antibiotic treatment.

15. The method of claim 8, wherein the composition comprises minerals, trace elements, vitamins, choline, taurine, carnitine, myo-inositol and/or mixtures thereof.

\* \* \* \* \*